United States Patent
Gkanatsios et al.

(10) Patent No.: US 12,146,933 B2
(45) Date of Patent: Nov. 19, 2024

(54) IMAGE IDENTIFICATION AND SELECTION FOR MOTION CORRECTION AND PEAK ENHANCEMENT

(71) Applicant: HOLOGIC, INC., Marlborough, MA (US)

(72) Inventors: Nikolaos Gkanatsios, Marlborough, MA (US); Jiachao Liang, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 462 days.

(21) Appl. No.: 17/436,536

(22) PCT Filed: Mar. 13, 2020

(86) PCT No.: PCT/US2020/022663
§ 371 (c)(1),
(2) Date: Sep. 3, 2021

(87) PCT Pub. No.: WO2020/186175
PCT Pub. Date: Sep. 17, 2020

(65) Prior Publication Data
US 2022/0171009 A1     Jun. 2, 2022

Related U.S. Application Data

(60) Provisional application No. 62/818,449, filed on Mar. 14, 2019.

(51) Int. Cl.
*G01R 33/565*     (2006.01)
*A61B 5/00*     (2006.01)
(Continued)

(52) U.S. Cl.
CPC ........ *G01R 33/56509* (2013.01); *A61B 5/004* (2013.01); *A61B 5/055* (2013.01);
(Continued)

(58) Field of Classification Search
CPC ... G01R 33/56509; G06T 7/337; G06T 7/248; G06T 19/20; G06T 2200/04;
(Continued)

(56) References Cited

U.S. PATENT DOCUMENTS 9,498,153 B2 * 11/2016 On .................. A61B 1/000095
2008/0097187 A1    4/2008 Gielen et al.
(Continued)

FOREIGN PATENT DOCUMENTS

JP     2010-514502     5/2010
JP     2013-039147     2/2013

OTHER PUBLICATIONS

PCT International Preliminary Report on Patentability in Application PCT/US2020/022663 mailed Sep. 23, 2021, 14 pages.
(Continued)

*Primary Examiner* — Gabriel I Garcia
(74) *Attorney, Agent, or Firm* — Merchant & Gould P.C.

(57) ABSTRACT

Methods and systems for performing motion correction on imaging data. The methods include accessing a set of imaging data. The set of imaging data includes first imaging data for a first time point, second imaging data for a second time point, and third imaging data for a third time point. A location of a region of interest (ROI) is identified in the different imaging data. Differences between the locations of ROI across the imaging data are determined and aggregated to generate an aggregate motion score for the respective imaging data in the set of imaging data. One of the imaging data is then selected as reference imaging data for motion correction based on the aggregate motion score. Motion correction of the set of imaging data is performed based on the selected reference imaging data. Similar comparisons on images may be performed for peak enhancement of MRI imaging data.

19 Claims, 9 Drawing Sheets

(51) Int. Cl.
  *A61B 5/055* (2006.01)
  *G06T 7/246* (2017.01)
  *G06T 7/33* (2017.01)
  *G06T 19/20* (2011.01)

(52) U.S. Cl.
  CPC .............. *G06T 7/248* (2017.01); *G06T 7/337* (2017.01); *G06T 19/20* (2013.01); *G06T 2200/04* (2013.01); *G06T 2207/10088* (2013.01); *G06T 2207/30068* (2013.01)

(58) Field of Classification Search
  CPC . G06T 2207/10088; G06T 2207/30068; A61B 5/004; A61B 5/055
  USPC ......................................................... 382/131
  See application file for complete search history.

(56) References Cited

U.S. PATENT DOCUMENTS

| | | |
|---|---|---|
| 2012/0121153 A1 | 5/2012 | Xue et al. |
| 2015/0091563 A1 | 4/2015 | Lu et al. |
| 2016/0292864 A1* | 10/2016 | Dabbah ................. A61B 5/004 |
| 2019/0059841 A1 | 2/2019 | Palma et al. |
| 2020/0029927 A1* | 1/2020 | Wilson ................. G01G 19/445 |
| 2021/0133954 A1* | 5/2021 | Melamed ............... G06N 20/00 |
| 2021/0225047 A1* | 7/2021 | Dryer .................... G06T 11/203 |

OTHER PUBLICATIONS

International Search Report and Written Opinion of the International Searching Authority for International Patent Application No. PCT/US2020/022663 mailed Aug. 10, 2020, 20 pages.

\* cited by examiner

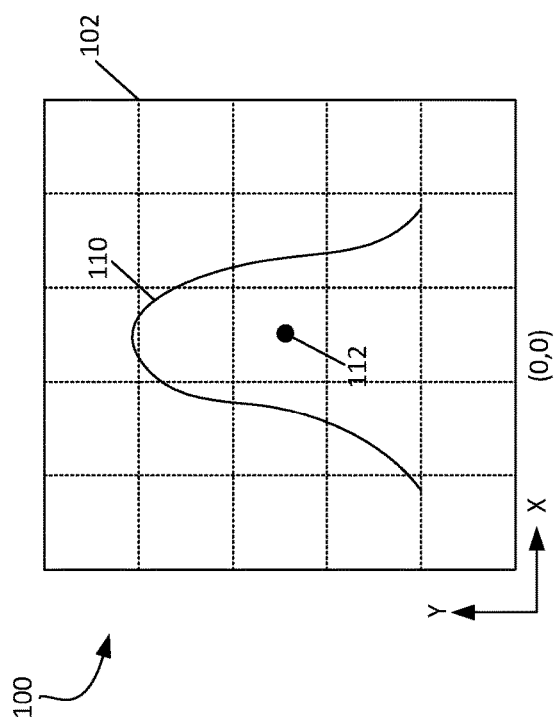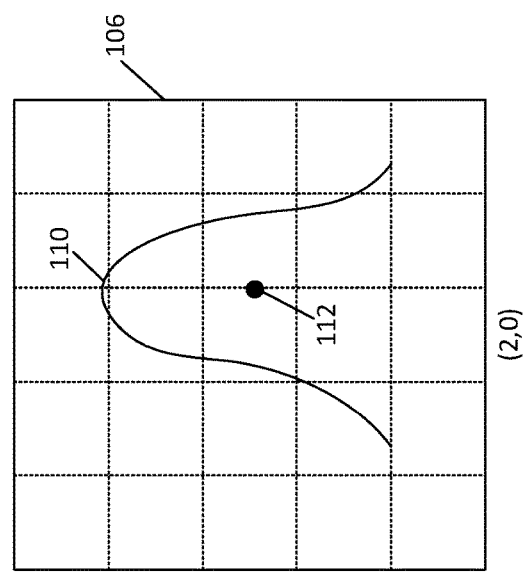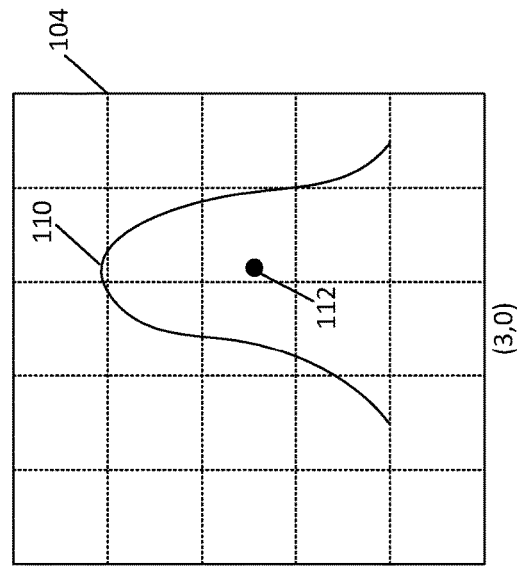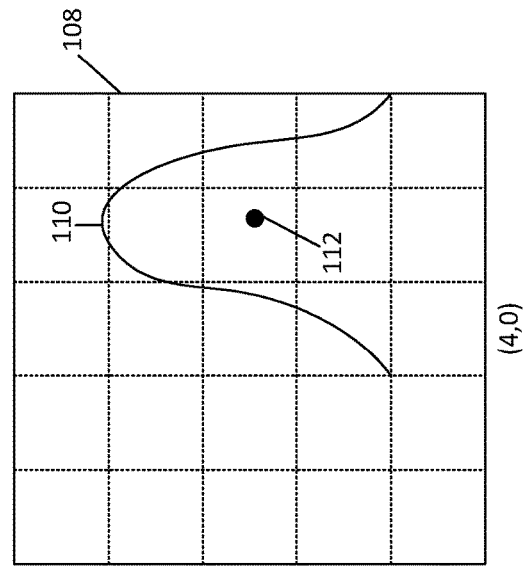
FIG. 1

400

Access a set of medical images

402

Identify a region of interest (ROI) in each of the medical images in the set of medical images

404

Identify a location of the ROI in each of the medical images in the set of medical images

406

Compare the identified locations of the ROI in a pair of the medical images of the set of medical images

408

Select the reference image for motion correction

410

Perform motion correction of the set of the medical images with the selected reference image.

412

Display motion corrected medical images

IMAGE IDENTIFICATION AND SELECTION FOR MOTION CORRECTION AND PEAK ENHANCEMENT

This application is a National Stage Application of PCT/US2020/022663, filed on Mar. 13, 2020, which claims the benefit of U.S. Patent Application Ser. No. 62/818,449, filed on Mar. 14, 2019, the disclosures of which is are hereby incorporated herein by reference their entireties. To the extent appropriate, a claim of priority is made to each of the above disclosed applications.

BACKGROUND

Medical imaging has become a widely used tool for identifying and diagnosing abnormalities, such as cancers or other conditions, within the human body. For example, magnetic resonance imaging (MRI) is one imaging modality that may be used for medical applications. In MRI, three dimensional (i.e., volumetric) imaging information of a patient's body region is acquired for diagnostic purposes. Other imaging modalities, such as computed tomography (CT), positron emission tomography (PET), mammography, and tomosynthesis, are also available for medical imaging procedures. In some imaging modalities, the images may be acquired at multiple points in time, often referred to as dynamic imaging. For instance, MRI information may be acquired at multiple points in time in order to study the time progression of dynamic processes, such as the movement of blood. Tomosynthesis involves acquiring images of a portion of the patient, such as the patient's breast, at multiple angles at different time points. In some instances, contrast-enhanced or dual-energy mammography may also involve acquiring images at multiple different time points. During such dynamic imaging procedures where images are acquired over time, the patient may move during the time required to complete the imaging procedure. If the patient moves during the imaging procedure, the acquired imaging data may need to be corrected to account for such movement of the patient.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for improving imaging procedures and resultant image quality from such imaging procedures. In an aspect, the technology relates to a method comprising accessing a set of imaging data including first imaging data for a first time point, second imaging data for a second time point, and third imaging data for a third time point. The method further includes identifying a first location of a region of interest (ROI) in the first imaging data; identifying a second location of the ROI in the second imaging data; and identifying a third location of the ROI in the third imaging data. The method also includes determining a plurality of differences between the identified locations, wherein the plurality of differences include a difference between: the first location and the second location; the first location and the third location; and the second location and the third location. The method additionally includes, based on the determined plurality of differences, selecting one of the first imaging data, the second imaging data, or the third imaging data as reference imaging data for motion correction, and performing motion correction for the set of imaging data with the selected reference image.

In an example, the set of imaging data is magnetic resonance imaging (MRI) data. In another example, the set of imaging data includes two-dimensional medical images and the locations of the ROI include a first coordinate corresponding to a first dimension and a second coordinate corresponding to a second dimension. In still another example, determining the difference between the first location and the second location comprises: determining the difference between the first coordinate of the first location and the first coordinate of the second location; and determining the difference between the second coordinate of the first location and the second coordinate of the second location. In yet another example, the set of imaging data includes three-dimensional medical images and the locations of the ROI include a first coordinate corresponding to a first dimension, and a second coordinate corresponding to a second dimension, and a second coordinate corresponding to a third dimension. In still yet another example, determining the difference between the first location and the second location comprises: determining the difference between the first coordinate of the first location and the first coordinate of the second location; determining the difference between the second coordinate of the first location and the second coordinate of the second location; and determining the difference between the third coordinate of the first location and the third coordinate of the second location. In another example, determining the difference between the first location and the second location comprises determining a distance between the first location and the second location.

In another aspect, the technology relates to a system comprising: a display; at least one processor; and memory storing instructions that, when executed by the at least one processor, cause the system to perform a set of operations. The set of operations includes accessing a set of imaging data including first imaging data for a first time point, second imaging data for a second time point, and third imaging data for a third time point; identifying a first location of a region of interest (ROI) in the first imaging data; identifying a second location of the ROI in the second imaging data; and identifying a third location of the ROI in the third imaging data. The set of operations also includes determining a plurality of differences between the identified locations, wherein the plurality of differences include a difference between: the first location and the second location; the first location and the third location; and the second location and the third location. The set of operations further includes based on the determined plurality of differences, selecting one of the first imaging data, the second imaging data, or the third imaging data as reference imaging data for motion correction; performing motion correction for the set of imaging data with the selected reference imaging data; and displaying at least a portion of the motion corrected set of imaging data on the display.

In an example, the system further includes a medical imaging apparatus and the set of operations further comprise acquiring the set of imaging data from the medical imaging apparatus. In another example, the medical imaging apparatus is a magnetic resonance imaging (MRI) machine and the imaging data includes MRI volumes. In still another example, the set of imaging data includes two-dimensional medical images and the locations of the ROI include a first coordinate corresponding to a first dimension and a second coordinate corresponding to a second dimension, and determining the difference between the first location and the second location comprises: determining the difference between the first coordinate of the first location and the first coordinate of the second location; and determining the difference between the second coordinate of the first location and the second coordinate of the second location. In yet another example, the medical images are three-dimensional medical images and the locations of the ROI include a first coordinate corresponding to a first dimension, and a second coordinate corresponding to a second dimension, and a second coordinate corresponding to a third dimension, and determining the difference between the first location and the second location comprises: determining the difference between the first coordinate of the first location and the first coordinate of the second location; determining the difference between the second coordinate of the first location and the second coordinate of the second location; and determining the difference between the third coordinate of the first location and the third coordinate of the second location. In still yet another example, determining the difference between the first location and the second location comprises determining a distance between the first location and the second location.

In another aspect, the technology relates to a method that includes accessing a set of medical images acquired at a plurality of time points. The method also includes identifying a region of interest (ROI) in at least half of the medical images in the set of medical images; identifying a location of the ROI in the at least half of the medical images in the set of medical images; comparing the identified locations of the ROI in at least one pair of the medical images of the set of medical images; based on the comparisons of the identified locations, selecting one of the medical images of the set of medical images to be a reference image for motion correction; and performing motion correction of the set of the medical images with the selected reference image.

In an example, the comparing operation comprises comparing the identified locations of the ROI in a plurality of pairs of medical images in the set of medical images. In another example, the plurality of pairs of medical images include all possible pairs of medical images in the set of medical images. In still another example, the medical images are two-dimensional medical images and the locations of the ROI include a first coordinate corresponding to a first dimension and a second coordinate corresponding to a second dimension. In yet another example, the medical images are three-dimensional medical images and the locations of the ROI include a first coordinate corresponding to a first dimension, and a second coordinate corresponding to a second dimension, and a second coordinate corresponding to a third dimension.

In another aspect, the technology relates to accessing a set of imaging data including first imaging data for a first time point, second imaging data for a second time point, and third imaging data for a third time point. The method also includes identifying a first location of a region of interest (ROI) in the first imaging data; identifying a second location of the ROI in the second imaging data; and identifying a third location of the ROI in the third imaging data. The method further includes determining a first difference between the first location and the second location; determining a second difference between the first location and the third location; and determining a third difference between the second location and the third location. The method also includes aggregating the first difference and the second difference to generate a first aggregate motion score for the first imaging data; aggregating the first difference and the third difference to generate a second aggregate motion score for the second imaging data; and aggregating the second difference and the third difference to generate a third aggregate motion score for the third imaging data. The method additionally includes, based on the first aggregate motion score, the second aggregate motion score, and the third aggregate motion score, selecting one of the first imaging data, the second imaging data, or the third imaging data as reference imaging data for motion correction; and performing motion correction of the set of imaging data based on the selected reference imaging data.

In an example, the first difference is a distance between the first location and the second location; the second difference is a distance between the first location and the third location; and the third difference is a distance between the second location and the third location. In another example, the first difference is an area between the first location and the second location; the second difference is an area between the first location and the third location; and the third difference is an area between the second location and the third location.

In another aspect, the technology relates to a method that includes accessing a set of imaging data including first imaging data for a first time point, second imaging data for a second time point, and third imaging data for a third time point; identifying an outline of a region of interest (ROI) in the first imaging data; identifying an outline of the ROI in the second imaging data; identifying an outline of the ROI in the third imaging data; determining a first area between the first outline and the second outline; determining a second area between the first outline and the third outline; determining a third area between the second outline and the third outline; aggregating the first area and the second area to generate a first aggregate motion score for the first imaging data; aggregating the first area and the third area to generate a second aggregate motion score for the second imaging data; aggregating the second area and the third area to generate a third aggregate motion score for the third imaging data; based on the first aggregate motion score, the second aggregate motion score, and the third aggregate motion score, selecting one of the first imaging data, the second imaging data, or the third imaging data as reference imaging data for motion correction; performing motion correction of the set of imaging data based on the selected reference imaging data; and displaying at least a portion of motion corrected set of imaging data.

In an example, the first area is a non-overlapping area between the first outline and the second outline; the second area is a non-overlapping area between the first outline and the third outline; and the third area is a non-overlapping area between the second outline and the third outline. In another example, selecting one of the first imaging data, the second imaging data, or the third imaging data as the reference imaging data for motion correction comprises selecting the imaging data with the lowest aggregate motion score. In still another example, the first area is an overlapping area between the first outline and the second outline; the second area is an overlapping area between the first outline and the third outline; and the third area is an overlapping area between the second outline and the third outline. In yet another example, selecting one of the first imaging data, the second imaging data, or the third imaging data as the reference imaging data for motion correction comprises selecting the imaging data with the highest aggregate motion score. In still yet another example, the ROI is a skin line of a breast.

In another example, the technology relates to a method the includes accessing a set of MRI imaging data, the set of MRI imaging data including at least a first volume acquired at a first time and a second volume acquired at a second time; identifying at least one local contrast enhancement region in the first volume; identifying the at least one local contrast enhancement region in the second volume; evaluating contrast dynamics for the local contrast enhancement region in the first volume; evaluating contrast dynamics for the local contrast enhancement region in the second volume; based on the evaluated contrast dynamics for the local contrast enhancement region in the first volume and the second volume, selecting either the first volume or the second volume as the peak enhancement volume; and performing the colorization for the set of MRI imaging data based on the peak enhancement volume.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

FIG. 1 depicts an example set of images acquired during a dynamic imaging procedure.

FIG. 4 depicts an example method for performing motion correction of medical images.

DETAILED DESCRIPTION

Figure 2A:
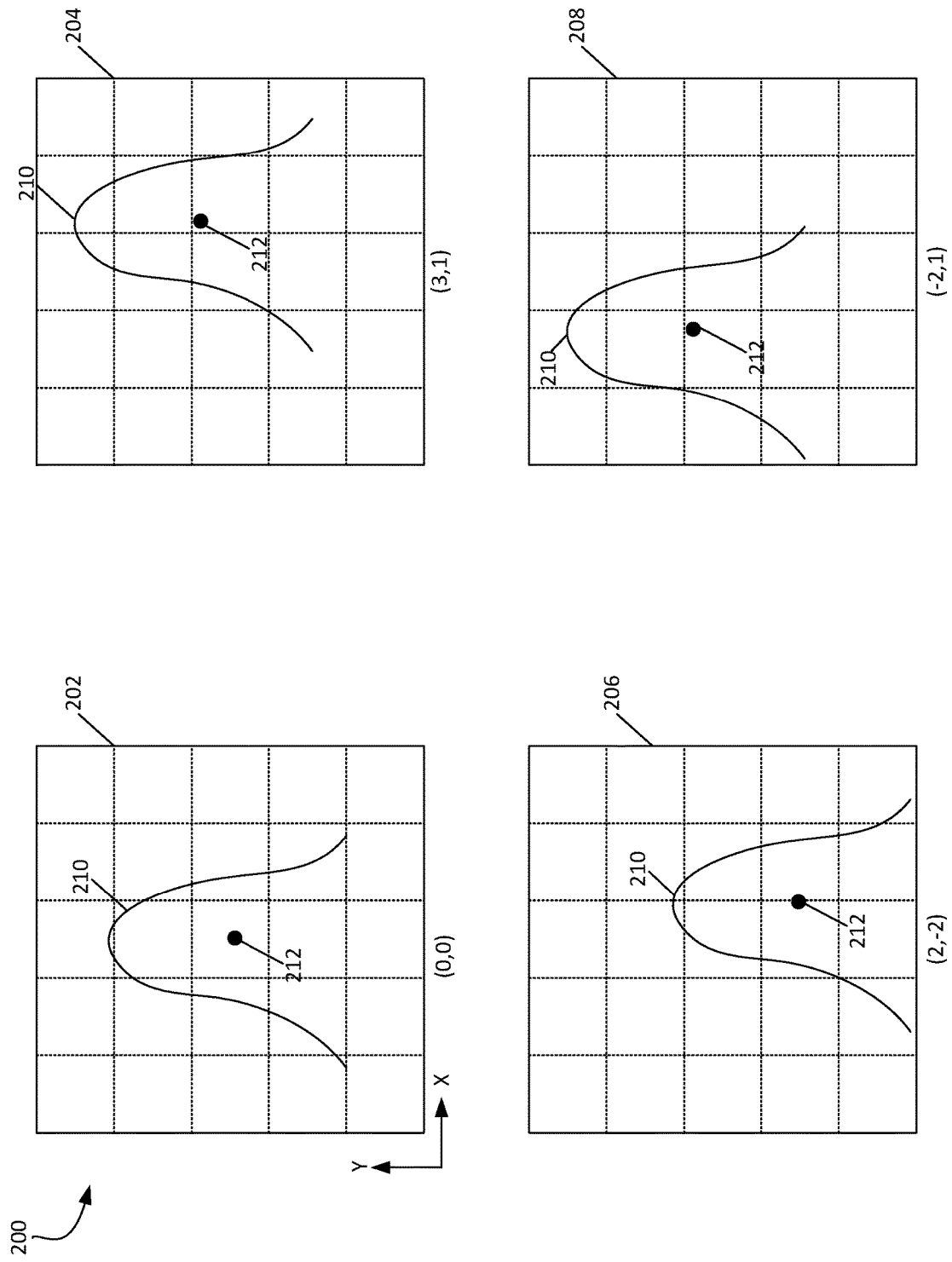
FIG. 2A depicts another example set of images acquired during a dynamic imaging procedure.

Dynamic imaging is a useful tool that acquires medical images at multiple points in time. These medical images may be acquired during a single scan or imaging procedure of the patient. For example, MRI images may be acquired in a series to study the time progression of dynamic processes, such as the movement of blood. Dynamic contrast enhanced (DCE) MRI is one such example of dynamic MRI imaging. In DCE MRI, multiple MRI volumes are acquired following the intravenous injection of a contrast agent. Each acquired volume shows how the contrast agent has progressed through the patient at the respective time point at which the volume was acquired. Tomosynthesis involves acquiring images of a portion of the patient, such as the patient's breast, at multiple angles at different time points. During such dynamic imaging procedures, the patient may move during the time required to complete the imaging procedure. Patient movement is also more likely where the duration of the scan is longer, and longer scans may also acquire more images than shorter scans. Each individual patient may also move in a different manner during his or her individual scan. Patient movement during any dynamic imaging procedure, however, often degrades the ultimate image quality of the images produced from the imaging procedure. For example, in DCE MRI, the dynamic processes that are intended to be seen may be more difficult to view as the multiple images are misaligned due to the movement of the patient.

Accordingly, it is desirable to have processes that allow for the images acquired during dynamic imaging procedures to be corrected for motion. In some motion correction algorithms, motion is corrected by shifting subsequent images to match the first image. For instance, in an example MRI procedure, four images may be acquired at different time points. To correct for motion during the procedure, the last three images may be shifted to align with the first image. Such a default process, however, may result to extensive correction of movement of the patient and may fail to account for different types of movement of the patient. Extensive motion correction to any image may reduce the resultant image quality and affect the potential clinical accuracy available from the image, particularly when diagnosing small lesions.

The present technology improves on such motion correction processes by accounting for the particular motion of the patient that has been imaged and reducing the total amount of motion correction that needs to be performed for a set of medical images. For instance, the present technology analyzes the locations of markers or regions of interest (ROIs) identified in each of the images acquired during a dynamic imaging procedure. As an example, the location of an ROI in a first image may be compared to the location of the ROI in each of the other acquired images. Similarly, the location of the ROI in a second image may be compared to the location of the ROI in each of the other acquired images. The comparison of ROI locations may involve determining a distance between the relative ROI locations in each respective image. Based on the comparisons of the ROI locations, one of the images is then selected as a reference, or base, image to perform the motion correction. For instance, the image that would reduce the total amount of image correction for entire set of images may be selected as the reference image for motion correction. The motion correction procedure is then performed using the selected image as the reference image, which results in less overall image correction required for dynamic imaging processes.

The present technology is also capable of analyzing multiple images or MRI volumes to identify most suitable volume to use as the peak enhancement volume for colorization of the portion of the patient being imaged, such as a breast. In general, colorization of breast MRI lesions is based on determining contrast dynamics within the imaged breast tissue prior to and the peak concentration of contrast has been achieved. In many current MRI colorization systems, a fixed timeout period, such as 120 seconds, is used to select the MRI volume. Thus, the same volume was always used as the peak enhancement volume. For instance, the volume acquired closest to the fixed timeout period was selected by default as the peak enhancement volume without any analysis of the volumes themselves. The timeout period, however, differs between different types of MRI imaging apparatuses, and the different types of MRI imaging apparatuses required different settings for the timeout period. That variability between imaging apparatuses also raised the potential to mislabel a volume as the peak enhancement volume, especially when taking into account the variability of tissue dynamics.

The present technology improves the peak volume selection process by actually analyzing the multiple MRI volumes acquired during a DCE MRI procedure. For instance, the present technology may evaluate the contrast dynamics of each acquired volume to more accurately select the volume that shows the peak enhancement properties. As such, the colorization and concentration curves for the set of MRI volumes may be based on a more accurate selection of a peak enhancement volume rather than a default time point.

FIG. 1 depicts an example set of images 100 acquired during a dynamic imaging procedure. The set of images 100 includes a first image 102 that was acquired at a first time point, a second image 104 that was acquired at a second time point, a third image 106 that was acquired at a third time point, and a fourth image 108 that was acquired at a fourth time point. Each image in the set includes a depiction of a breast 110. A region of interest (ROI) 112 has also been identified in each of the images. In the example depicted, the ROI is the centroid of the breast 110. The ROI, however, may be different in other examples and may be any identifiable feature of the breast or portion of the patient that is being imaged. In examples where a breast is imaged, the ROI may be the skin line, the nipple, chest wall, or other fiduciary markers. As can be seen from the set of images 100, the breast 110 and the region of interest has moved in each of the images. Accordingly, the patient has moved between the time the first image 102 was acquired and the time the fourth image 108 was acquired, and some form of motion correction is desired.

The present technology identifies the most appropriate image of the set of images 100 to be used as the reference image for motion correction processes. For example, the reference image is the image to which the remaining references are altered to match, or at least be altered to move closer to the position of the breast 110 in the reference image. To select the reference image, an analysis of the locations of the ROI 112 across the images is performed.

In the example depicted, the ROI 112 in the first image is located at an x-coordinate of 0 and a y-coordinate of 0. Typical coordinate notation of (x,y) may be used herein. As such, the location of the ROI 112 in the first image 102 may be referred to as (x1, y1) and has a value of (0,0). The location of the RO1 112 in the second image 104 is represented as (x2, y2) and has a value of (3,0). The location of the ROI 112 in the third image 106 is represented as (x3, y3) and has a value of (2,0), and the location of the ROI 112 in the fourth image 108 is (x4, y4) and has a value of (4,0). Accordingly, in the example depicted, the breast 112 shifted only in the x-direction.

To determine which image of the set of images 100 is best suited to be selected as the reference image, a comparison of the location of the ROI 112 in each image is compared to location of the ROI 112 in the remaining image. The comparisons may be used or aggregated to determine an aggregate motion score for each of the images. The image of the set of images 100 that has the lowest aggregate motion score may be selected as the reference image.

To determine the aggregate motion score for the first image 102, the difference between the location of the ROI 112 in the first image 102 and the locations of the ROI 112 in the remaining images is determined. For instance, the differences and the aggregate motion score for the first image 102 are as follows:

TABLE 1

First Image Analysis

| Comparison | Representative Equation | Resultant Value |
|---|---|---|
| First Image vs. Second Image | $x_1 - x_2$ | 3 |
| First Image vs. Third Image | $x_1 - x_3$ | 2 |
| First Image vs. Fourth Image | $x_1 - x_4$ | 4 |
| Aggregate Motion Score for First Image | | 9 |

As can be seen from the above table, the aggregate motion score for the first image is the sum or aggregation of the differences in location of the ROI 112 between the first image 102 and the remaining images. Of note, in the example depicted, because there was no movement in the y-direction of the breast 110, calculations regarding the y-coordinate have been omitted as each of the differences would have been zero. In addition, the differences in the present example are generally taken as the absolute value of the differences such that negative values may be avoided.

The differences and the aggregate motion score for the second image 104 are as follows:

TABLE 2

Second Image Analysis

| Comparison | Representative Equation | Resultant Value |
|---|---|---|
| Second Image vs. First Image | $x_2 - x_1$ | 3 |
| Second Image vs. Third Image | $x_2 - x_3$ | 1 |
| Second Image vs. Fourth Image | $x_2 - x_4$ | 1 |
| Aggregate Motion Score for Second Image | | 5 |

The differences and the aggregate motion score for the third image 106 are as follows:

TABLE 3

Third Image Analysis

| Comparison | Representative Equation | Resultant Value |
|---|---|---|
| Third Image vs. First Image | $x_3 - x_1$ | 2 |
| Third Image vs. Second Image | $x_3 - x_2$ | 1 |
| Third Image vs. Fourth Image | $x_3 - x_4$ | 2 |
| Aggregate Motion Score for Third Image | | 5 |

The differences and the aggregate motion score for the fourth image 108 are as follows:

TABLE 4

Fourth Image Analysis

| Comparison | Representative Equation | Resultant Value |
|---|---|---|
| Fourth Image vs. First Image | $x_4 - x_1$ | 4 |
| Fourth Image vs. Second Image | $x_4 - x_2$ | 1 |
| Fourth Image vs. Third Image | $x_4 - x_3$ | 2 |
| Aggregate Motion Score for Fourth Image | | 7 |

The following table provides a summary of each of the aggregate motion scores:

TABLE 5

Aggregate Motion Score Summary of Tables 1-4

| Image Number | Aggregate Motion Score |
|---|---|
| First Image | 9 |
| Second Image | 5 |
| Third Image | 5 |
| Fourth Image | 7 |

Accordingly, the second image 104 and third image 106 have the lowest aggregate motion scores (5), followed by the fourth image 108, with an aggregate motion score of 7, and the first image 102 with an aggregate motion score of 9. Thus, in this example, one of the second image 104 or the third image 108 is selected as the representative image for motion correction. In some examples, such as the present example, there is a tie between two images for the lowest aggregate motion scores. To break the tie, a maximum difference between any pair may be utilized. For instance, in the present example, the calculated differences for the second image 104 were 3, 1, and 1. The calculated differences for the third image 106 were 2, 1, and 2. Therefore, the maximum difference for the second image was 3 and the maximum difference for the third image was 2. The image having the lowest maximum difference is selected as the reference image for motion correction. Consequently, in the present example, the third image 106 is selected as the reference. It is worth noting that, based on the aggregate motion scores, the first image 102 would have been the worst selection for use as a reference image because using the first image would have required the most amount of motion correction across the set of images 100. As such, the analysis of the multiple pairs of images within the set of images 100 allows for an identification of a reference image that requires less than motion correction than if an arbitrary reference image was selected, which results in improved image quality of the set of images 100 after motion correction. The analysis or more pairs of images may also result in improved accuracy in the selection of the most appropriate image for use as the reference image.

FIG. 2 depicts another depicts an example set of images 200 acquired during a dynamic imaging procedure. The set of images 200 includes a first image 202 that was acquired at a first time point, a second image 204 that was acquired at a second time point, a third image 206 that was acquired at a third time point, and a fourth image 208 that was acquired at a fourth time point. Each image in the set includes a depiction of a breast 210. An ROI 212 has also been identified in each of the images. In the example depicted, the ROI is the centroid of the breast 210. As can be seen from the set of images 200, the breast 210 and the region of interest has moved in each of the images. The example depicted in FIG. 2 differs from the example depicted in FIG. 2 in that the breast 210 movement in FIG. 2 is in two dimensions.

In the example depicted in FIG. 2, the ROI 212 in the first image is located at (0,0). The location of the ROI 212 in the second image 204 is (3,1), the location of the ROI 212 in the third image 206 is (2,−2), and the location of the ROI 212 in the fourth image 208 is (−2, 1). Determining the difference between each of the pairs of images in the set of images 200 may be performed by calculated the distance from the ROI 212 locations in each of the images. One example equation for calculating the distance between two ROI 212 locations is as follows:

$$D = \sqrt{(x_1 - x_2)^2 + (y_1 - y_2)^2}$$

In the above equation, D is the distance, $x_1$ is x-coordinate of a first ROI 212 location, $y_1$ is the y-coordinate of the first ROI 212 location, $x_2$ is the x-coordinate of a second ROI 212 location, and $y_2$ is the y-coordinate of the second ROI 212 location. Of note, the above distance equation could have been used to calculate distance in the example in FIG. 1, and the same results would have been achieved.

The differences and the aggregated motion score for the first image 202 are thus as follows:

TABLE 6

First Image Analysis

| Comparison | Representative Equation | Resultant Value |
|---|---|---|
| First Image vs. Second Image | $\sqrt{(x_1 - x_2)^2 + (y_1 - y_2)^2}$ | 3.16 |
| First Image vs. Third Image | $\sqrt{(x_1 - x_3)^2 + (y_1 - y_3)^2}$ | 2.83 |
| First Image vs. Fourth Image | $\sqrt{(x_1 - x_4)^2 + (y_1 - y_4)^2}$ | 2.23 |
| Aggregate Motion Score for First Image | | 8.22 |

The differences and the aggregate motion score for the second image 204 are as follows:

TABLE 7

Second Image Analysis

| Comparison | Representative Equation | Resultant Value |
|---|---|---|
| Second Image vs. First Image | $\sqrt{(x_2 - x_1)^2 + (y_2 - y_1)^2}$ | 3.16 |
| Second Image vs. Third Image | $\sqrt{(x_2 - x_3)^2 + (y_2 - y_3)^2}$ | 3.16 |
| Second Image vs. Fourth Image | $\sqrt{(x_2 - x_4)^2 + (y_2 - y_4)^2}$ | 5 |
| Aggregate Motion Score for Second Image | | 11.32 |

The differences and the aggregate motion score for the third image 206 are as follows:

TABLE 8

Third Image Analysis

| Comparison | Representative Equation | Resultant Value |
|---|---|---|
| Third Image vs. First Image | $\sqrt{(x_3 - x_1)^2 + (y_3 - y_1)^2}$ | 2.82 |
| Third Image vs. Second Image | $\sqrt{(x_3 - x_2)^2 + (y_3 - y_2)^2}$ | 3.16 |
| Third Image vs. Fourth Image | $\sqrt{(x_3 - x_4)^2 + (y_3 - y_4)^2}$ | 5 |
| Aggregate Motion Score for Third Image | | 10.98 |

The differences and the aggregate motion score for the fourth image 208 are as follows:

TABLE 9

Fourth Image Analysis

| Comparison | Representative Equation | Resultant Value |
| --- | --- | --- |
| Fourth Image vs. First Image | $\sqrt{(x_4 - x_1)^2 + (y_4 - y_1)^2}$ | 2.23 |
| Fourth Image vs. Second Image | $\sqrt{(x_4 - x_2)^2 + (y_4 - y_2)^2}$ | 5 |
| Fourth Image vs. Third Image | $\sqrt{(x_4 - x_3)^2 + (y_4 - y_3)^2}$ | 5 |
| Aggregate Motion Score for Fourth Image | | 10.23 |

The following table provides a summary of each of the aggregate motion scores:

TABLE 10

Aggregate Motion Score Summary of Tables 6-9

| Image Number | Aggregate Motion Score |
| --- | --- |
| First Image | 8.22 |
| Second Image | 11.32 |
| Third Image | 10.98 |
| Fourth Image | 10.23 |

As can be seen from the above table, the first image 102 has the lowest aggregate motion score. Thus, the first image 102 is selected as the reference image for motion correction.

Figure 2C:
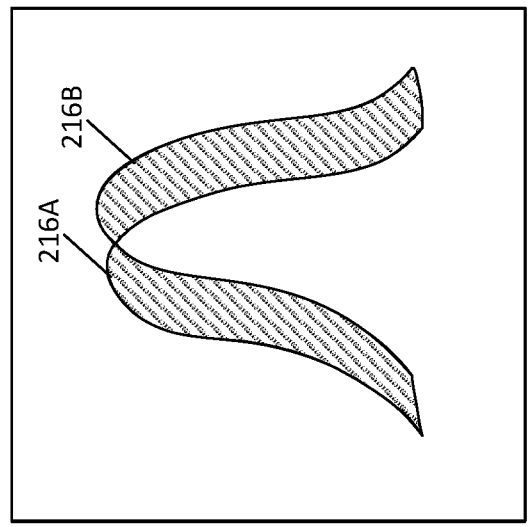
FIG. 2C depicts an example of the non-overlapping area between two outlines of a skin line of a breast.
Figure 2B:
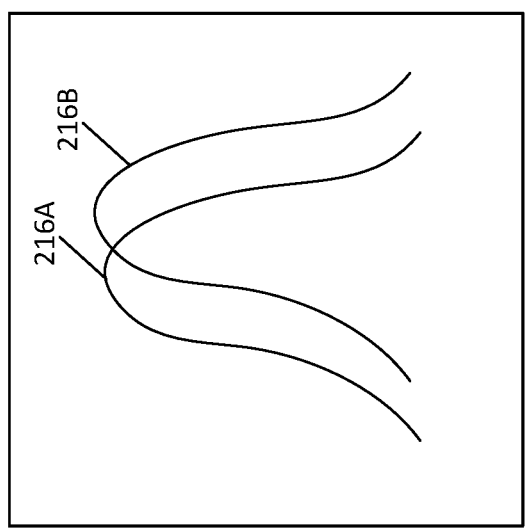
FIG. 2B depicts a difference in regions of interest (ROIs) in two images.

FIG. 2B depicts a difference in ROIs in two images. In particular, an outline of the skin line 216A of the breast 210 from image 202 is shown overlaid on top of an outline of the skin line 216B of the breast 210 from image 204 depicted in FIG. 2A. In some examples, the present technology may use the outline of an ROI, such as the skin line of a breast, the chest wall, or other identifiable markers having outlines, to determine the differences between the locations of the ROI in each of the images. Determining the difference between two outlines may include determining the area that are not common to both outlines. FIG. 2C depicts an example of the area between two outlines of a skin line of a breast. The area that is not common, or overlapping, is designated by the hashed lines. That non-overlapping area may be determined for each pair of images in a set of images. The determination of the non-overlapping area may be made by overlaying the two outlines and calculating the areas in the outlines that do not overlap. Such a determination may be made through image analysis processes. The area may also be determined by representing each outline as a curve or function and then taking the integral between the difference in the two curve or functions. For example, for the pair of outlines 216A, 216B represented in FIGS. 2B-2C, the first outline 216A may be represented as a first function $f(x)$ and the second outline 216B may be represented as a second function $g(x)$. The area between the two functions may be determined by taking the integral of the difference of the two functions, such as $\int (f(x) - g(x))dx$. Depending on the implementation, an integral may need to be calculated between each intersection point of the two functions to determine the total area.

For each image, an aggregate motion score may also be calculated that is based on an aggregate of the differences in areas for each pair of images. Such a determination is similar to aggregate motion scores discussed above that related to determining the distance between two points. In examples where an outline of an ROI is used, the aggregate motion score may be based on the areas between the two outlines. The image with the lowest aggregate motion score is then selected as the reference image for performing motion correction.

As should be appreciated, while the above examples set of images include only four images, the process for selecting the most appropriate reference image for motion correction may be applied to sets of images having a greater or fewer number of references. As an example, for each image in a set of images (no matter the number of images), the difference between the locations of the ROI for each possible pair of images in the set may be determined. The differences may be then be aggregated to determine an aggregate motion score for each image in the set of images. The image with the lowest aggregate motion score is then selected as the reference image for motion correction.

In addition, in the above examples in FIG. 1 and FIG. 2A-C, the sets of images have been two-dimensional images. For instance, the images may be representative of slices from an MRI volume. The first image may be a slice from a first MRI volume taken at the first time point, the second image may be a slice from a second MRI volume taken at the second time point, the third image may be a slice from a third MRI volume taken at the third time point, and the fourth image may be a slice from the fourth MRI volume taken at the fourth time point. When the particular image is selected as the reference image, the entire corresponding volume may be selected as the reference volume for performing motion correction. For example, if the third image is selected as the reference image, the MRI volume acquired at the third time point may be selected as the reference volume for performing motion correction.

In other examples, analysis and comparison of ROI locations may be done across three-dimensional images or image data. For instance, a three dimensional location of an ROI may be identified in a first volume and locations of the ROI may be identified in other volumes. The location of the ROI may be represented in three-dimensional Cartesian coordinates (x, y, z). The location of the ROI in a first volume may then be represented as $(x_1, y_1, z_1)$ and the location of the ROI in a second volume may be represented as $(x_2, y_2, z_2)$. The distance between two locations of an ROI may be determined with the following equation:

$$D = \sqrt{(x_1 - x_2)^2 + (y_1 - y_2)^2 + (z_1 - z_2)^2}$$

As in the above examples, a difference between the locations of the ROI may be determined for all possible pairs of volumes in a set of volumes. The differences for each volume may be aggregated to determine an aggregate motion score for each of the volumes, and the volume with the lowest aggregate motion score is selected as the reference volume for motion correction.

Further, while in the examples above only a single ROI was identified, in other examples multiple ROIs in each image may be identified. For example, a first ROI may be identified and a second ROI may be identified in each image. The process for determining the difference between the locations of the first ROI and the calculation of the differences of the locations may be determined as discussed above. The same process may then be performed for the second ROI. The aggregate motion score for each image may then be a combination of the determined differences for the first ROI and the second ROI.

Figure 3:
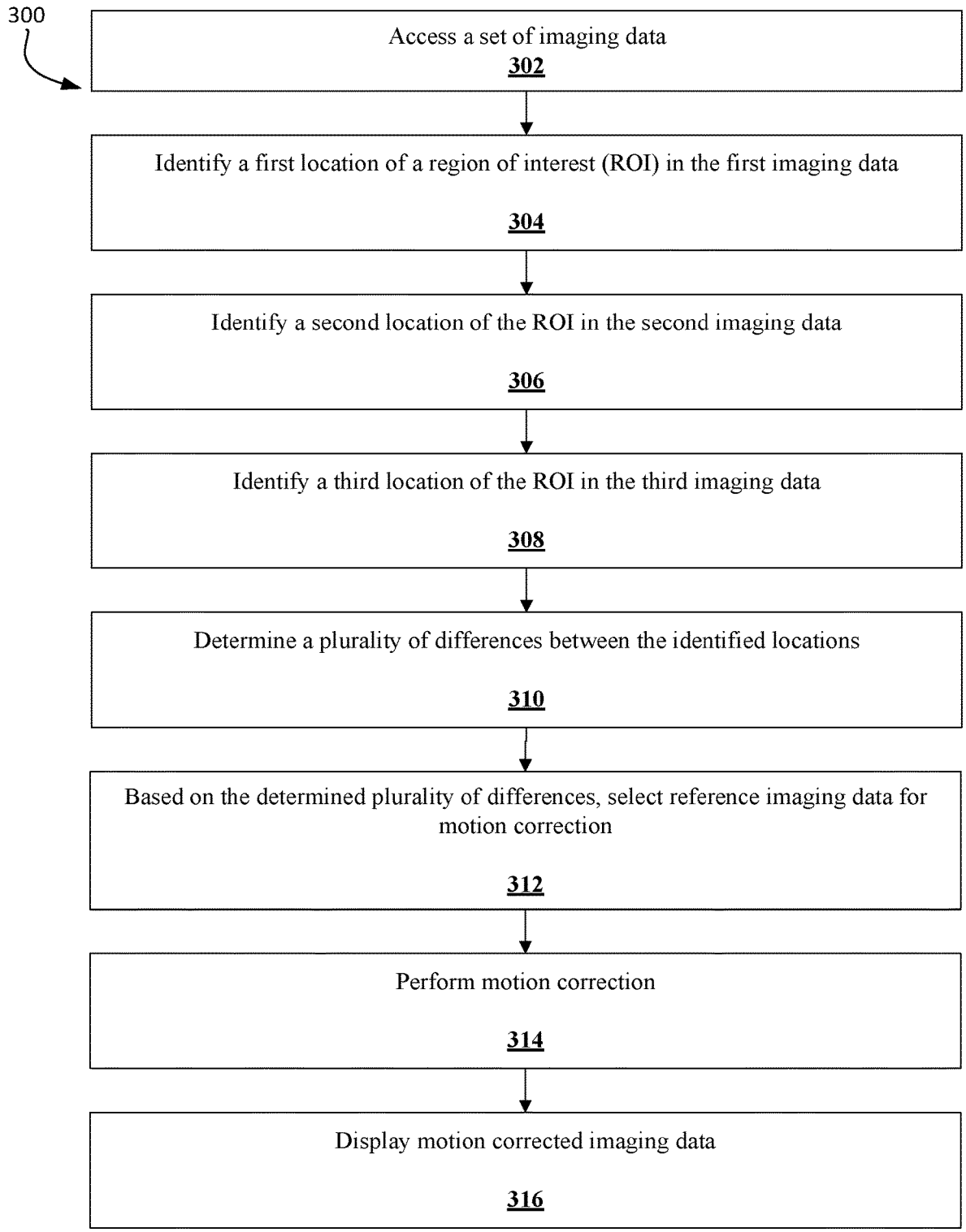
FIG. 3 depicts an example method for performing motion correction of medical images.

FIG. 3 depicts an example method 300 for performing motion correction of medical images. At operation 302, a set of imaging data is accessed. Accessing the set of imaging data may include acquiring the images from a medical imaging apparatus and/or receiving the medical images from another storage source. The set of imaging data may include first imaging data for a first time point, second imaging data for a second time point, and third imaging data for a third time point. Additional imaging date may also be included in the set of imaging data. The set of imaging data may include, for example, MRI imaging data such as MRI volumes and/or slices of MRI volumes. At operation 304, a first location of an ROI in the first imaging data is identified. The identification of an ROI in the imaging data may be performed via computer-aided detection that analyzes the imaging data to identify the particular ROI in the imaging data and determine its location and coordinates. At operation 306, a second location for the ROI in the second imaging data is identified, and at operation 308, a third location of the ROI is identified in the third imaging data. The second location of the ROI is the location of the ROI in the second imaging data. Similarly, the third location of the ROI is the location of the ROI in the third imaging data. In some examples, the set of imaging data includes two-dimensional medical images and the locations of the ROI include a first coordinate corresponding to a first dimension (e.g., the x dimension) and a second coordinate corresponding to a second dimension (e.g., they dimension). For instance, the locations of the ROI may be represented as coordinates such as (x, y). In other examples, the set of imaging data may include three-dimensional medical images, and the locations of the ROI include a first coordinate corresponding to a first dimension (e.g., the x dimension), and a second coordinate corresponding to a second dimension (e.g., the y-dimension), and a second coordinate corresponding to a third dimension (e.g., the z dimension). For instance, the locations of the ROI may be represented as coordinates such as (x, y, z). The differences determined may be distances from one location to another, and such distances may be calculated or determined using the above distance equations.

At operation 310, a plurality of differences between the identified locations of the ROI are determined. For instance, the difference between (1) the first location and the second location, (2) the first location and the third location, and (3) the second location and the third location may all be determined. As an example, where the set of imaging data includes two-dimensional images, determining the difference between the first location and the second location may include determining the difference between the first coordinate of the first location and the first coordinate of the second location, and determining the difference between the second coordinate of the first location and the second coordinate of the second location. In an example where the set of imaging data includes three-dimensional images, determining the difference between the first location and the second location may include determining the difference between the first coordinate of the first location and the first coordinate of the second location, determining the difference between the second coordinate of the first location and the second coordinate of the second location, and determining the difference between the third coordinate of the first location and the third coordinate of the second location.

Based on the determined plurality of differences in operation 310, the reference imaging data is selected at operation 312. For instance, either the first imaging data, the second imaging data, or the third imaging data is selected to be the reference imaging data for motion correction. The determination may be based on an aggregate motion score for each of the imaging data, and that aggregate motion score is based on the determined plurality of differences. At operation 314, motion correction is performed based on the imaging data selected as the reference imaging data in operation 312. For example, the imaging data other than the selected imaging data may be altered to more closely match the selected imaging data. Performing the motion correction may result in a motion-corrected set of imaging data. At operation 316, at least a portion of the motion-corrected set of imaging data may be displayed. The motion-corrected set of imaging data may also be stored locally or remotely. The motion-corrected set of imaging data may also be used in completing or performing the clinical task or review for which the imaging procedure was performed. The motion-corrected set of imaging data may also be used for computing or generating final images, such as in MRI or tomosynthesis procedures. For instance, a reconstruction of a tomosynthesis volume may be generated from the motion-corrected set of imaging data and/or tomosynthesis slices may be generated from the motion-corrected set of imaging data.

FIG. 4 depicts another method 400 for performing motion correction. At operation 402, a set of medical images is accessed. The set of medical images includes medical images that were acquired at a plurality of different time points. At operation 404, an ROI is identified in each of the medical images in the set of medical images. In some examples, the ROI may be identified in at least a majority, or about half, of the medical images in the set of medical images. At operation 406, a location of the ROI in each of the medical images is identified. In some examples, the location of the ROI is identified for each image where the ROI was identified in operation 404. The identification of the ROI and the identification of the location of the ROI may be performed using computer-aided detection.

At operation 408, the locations of the ROI identified at operation 406 are compared. As an example, the locations of the ROI in at least one pair of medical images are be compared. In other examples, the location of the ROI may be compared for a plurality of pairs of medical images in the set of medical images. For instance, the plurality of pairs may include all possible pairs of medical images in the set of medical images. At operation 410, the reference image for motion correction is selected based on the comparisons of the locations of the ROI in operation 408. At operation 412, motion correction is performed on the set of medical images based on the set of medical images. Performing the motion correction may result in a motion-corrected set of medical images. At operation 414, at least a portion of the motion-corrected set of medical images may be displayed. The motion-corrected set of medical images may also be stored locally or remotely. The motion-corrected set of imaging data may also be used in completing or performing the clinical task or review for which the imaging procedure was performed. The motion-corrected set of imaging data may also be used for computing or generating final images, such as in MRI or tomosynthesis procedures. For instance, a reconstruction of a tomosynthesis volume may be generated from the motion-corrected set of imaging data and/or tomosynthesis slices may be generated from the motion-corrected set of imaging data.

Figure 5A:
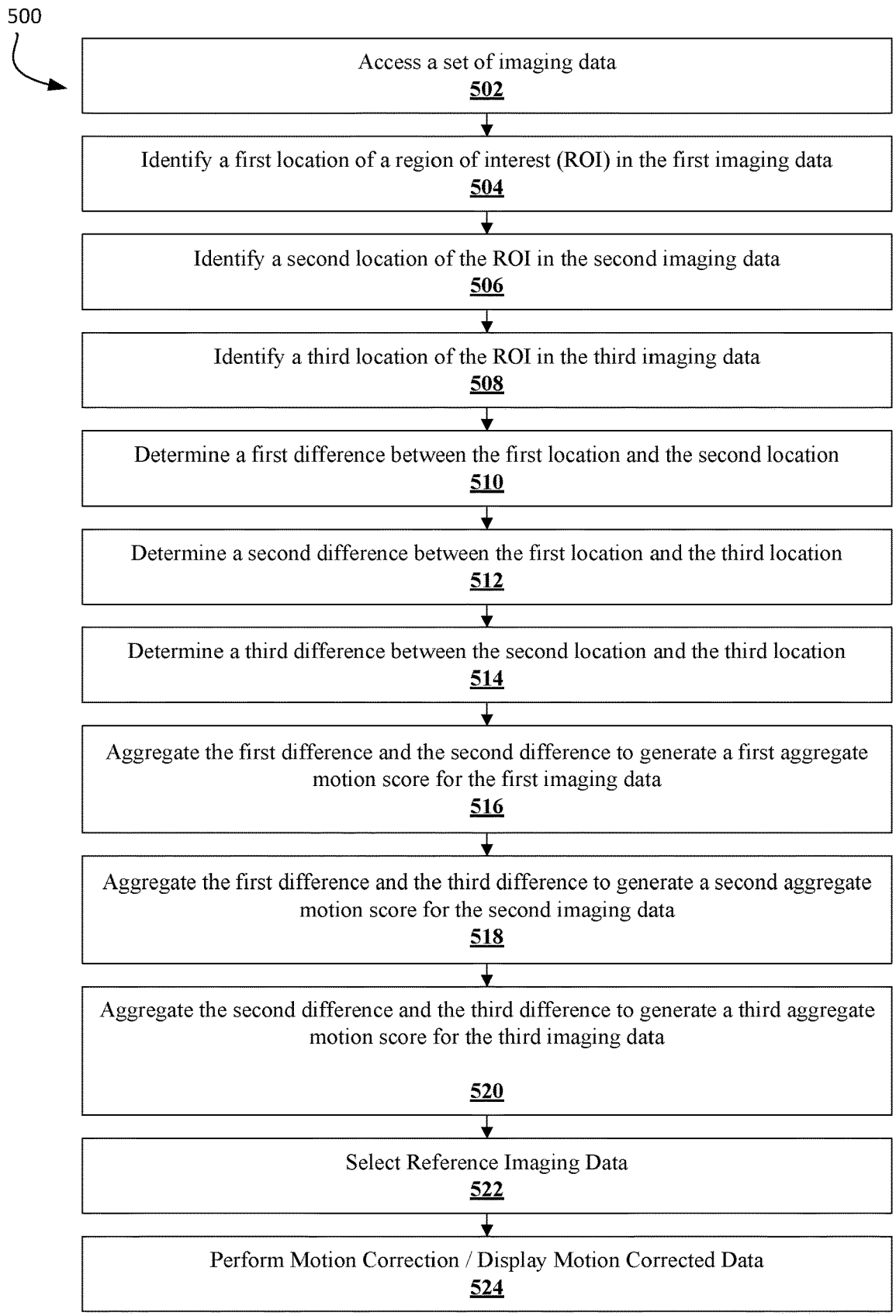
FIGS. 5A and 5B depict an example method for performing motion correction of medical images.

FIG. 5A depicts another method 500 for performing motion correction. At operation 502, a set of imaging data is accessed. The imaging data includes at least first imaging data for a first time point, second imaging data for a second time point, and third imaging data for a third time point. At operation 504, a first location of an ROI is identified in the first imaging data. At operation 506, a second location of an ROI is identified in the second imaging data. At operation 508, a third location of the ROI is identified in the third imaging data.

At operation 510, a first difference is determined between the first location and the second location. At operation 512, a second difference is determined between the first location and the third location. At operation 514, a third difference is determined between the second location and the third location. At operation 516, the first difference and the second difference are aggregated to generate a first aggregate motion score for the first imaging data. At operation 518, the first difference and the third difference are aggregated to generate a second aggregate motion score for the second imaging data. At operation 520, the second difference and the third difference are aggregated to generate a third aggregate motion score for the third imaging data.

At operation 522, reference imaging data is selected based on the first composite motion score, the second composite motion score, and the third composite motion score. For instance, the imaging data that has the lowest aggregate motion score may be selected as the reference imaging data for motion correction. Thus, one of the first imaging data, the second imaging data, or the third imaging data as reference imaging data for motion correction in operation 522. At operation 524, motion correction is performed on the set of imaging data based on the selected reference imaging data. The motion corrected imaging data may also then be displayed.

Figure 5B:
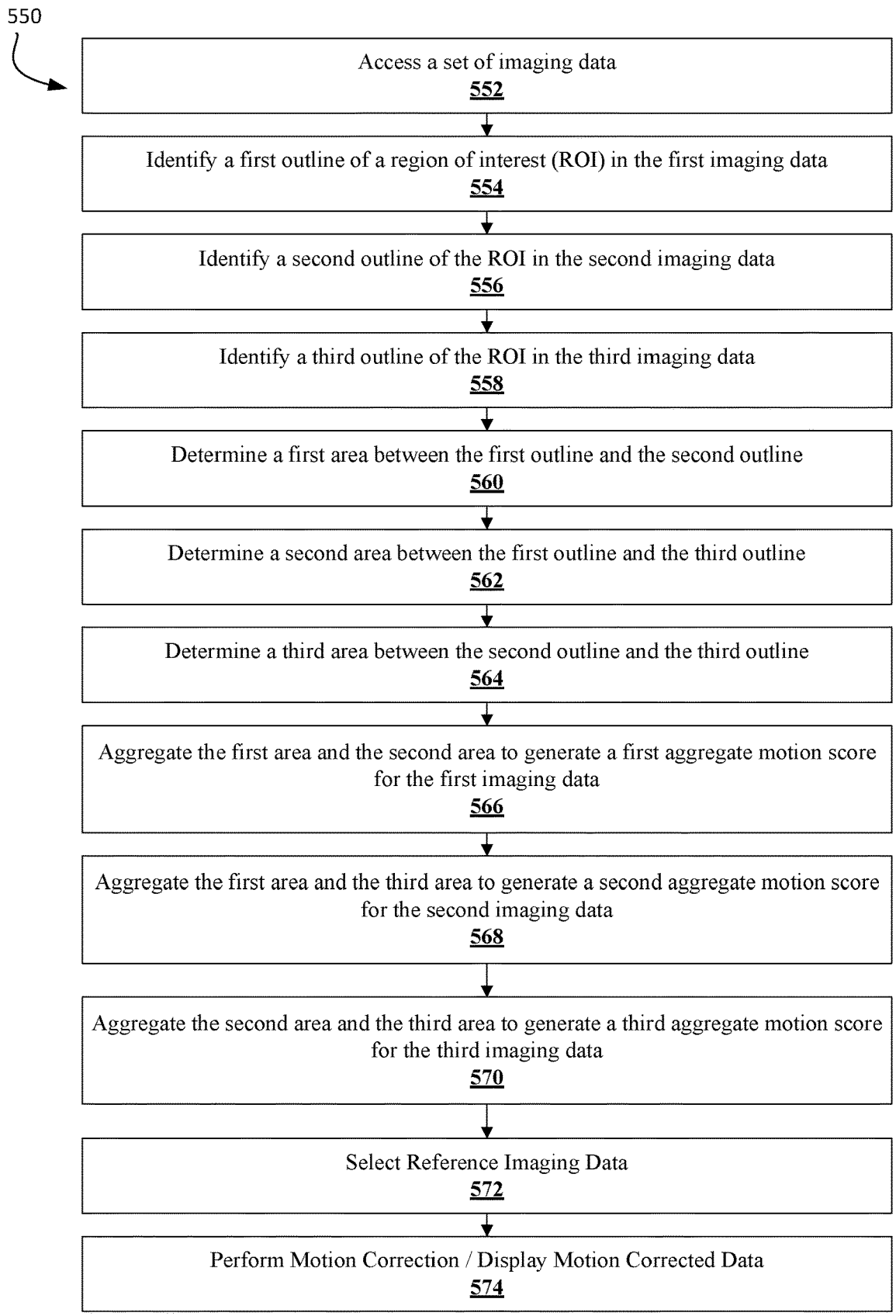

FIG. 5B depicts another method 550 for performing motion correction. At operation 552, a set of imaging data is accessed. The imaging data includes at least first imaging data for a first time point, second imaging data for a second time point, and third imaging data for a third time point. At operation 554, a first outline of an ROI is identified in the first imaging data. At operation 556, a second outline of an ROI is identified in the second imaging data. At operation 558, a third outline of the ROI is identified in the third imaging data.

At operation 560, a first area is determined between the first outline and the second outline. The area determined may be the non-overlapping area between the first outline and the second outline when the first imaging data and the second imaging data are overlaid. In other examples, the area determined may be the overlapping area between the first outline and the second outline when the first imaging data and the second imaging data are overlaid. At operation 562, a second area is determined between the first outline and the third outline. At operation 564, a third area is determined between the second outline and the third outline. At operation 566, the first area and the second area are aggregated to generate a first aggregate motion score for the first imaging data. At operation 568, the first area and the third area are aggregated to generate a second aggregate motion score for the second imaging data. At operation 570, the second area and the third area are aggregated to generate a third aggregate motion score for the third imaging data.

At operation 572, reference imaging data is selected based on the first composite motion score, the second composite motion score, and the third composite motion score. For instance, in examples where the areas determined in operations 560-564 are the non-overlapping areas of the respective outlines, the imaging data that has the lowest aggregate motion score may be selected as the reference imaging data for motion correction. In examples where the areas determined in operations 560-564 are the overlapping areas of the respective outlines, the imaging data that has the highest aggregate motion score may be selected as the reference imaging data for motion correction. Thus, one of the first imaging data, the second imaging data, or the third imaging data as reference imaging data for motion correction in operation 572. At operation 574, motion correction is performed on the set of imaging data based on the selected reference imaging data. The motion corrected imaging data may also then be displayed. The motion-corrected set of imaging data may also be used in completing or performing the clinical task or review for which the imaging procedure was performed. The motion-corrected set of imaging data may also be used for computing or generating final images, such as in MRI or tomosynthesis procedures. For instance, a reconstruction of a tomosynthesis volume may be generated from the motion-corrected set of imaging data and/or tomosynthesis slices may be generated from the motion-corrected set of imaging data.

Figure 6:
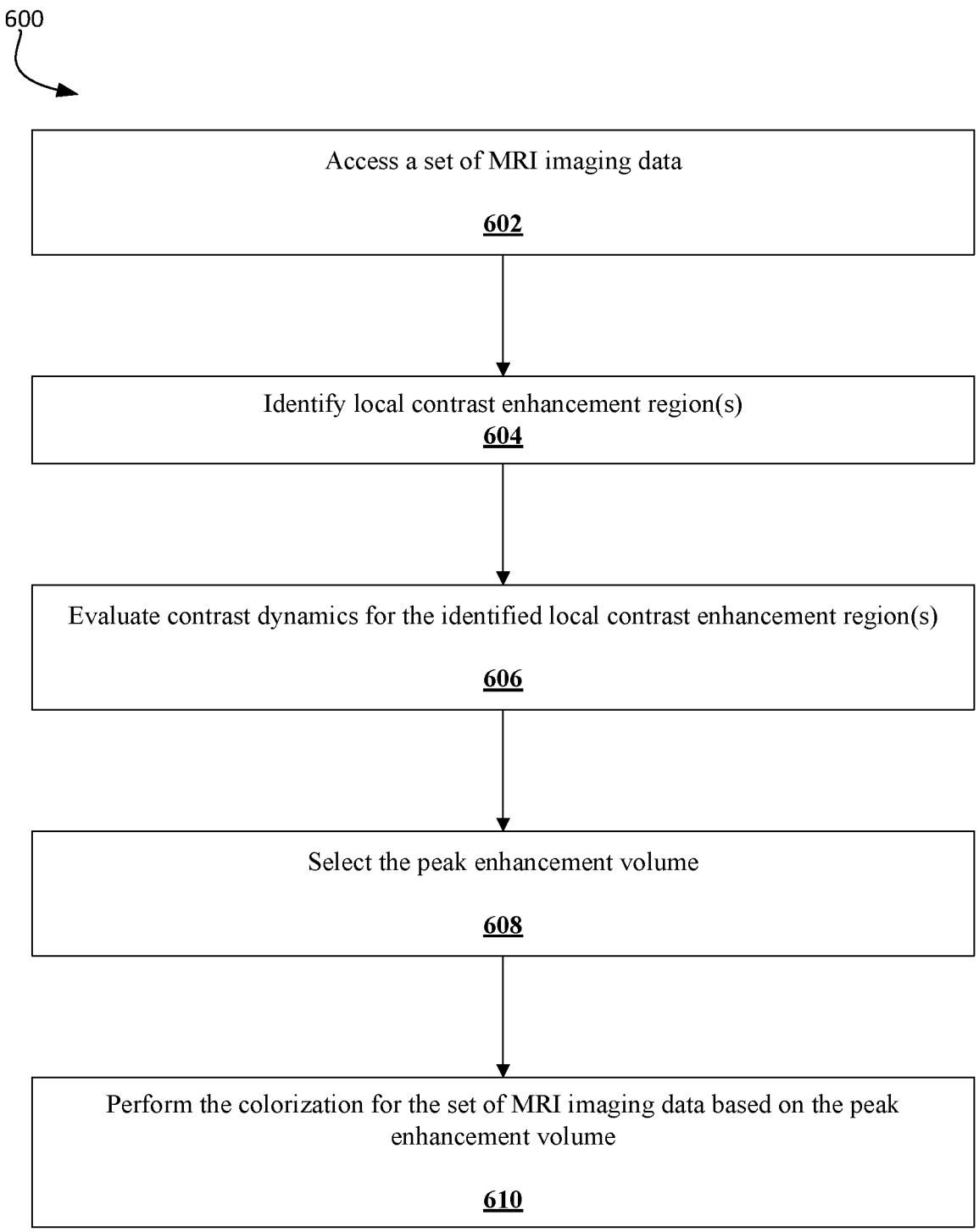
FIG. 6 depicts an example method for performing colorization of MRI images.

FIG. 6 depicts an example method for performing colorization of MRI images. At operation 602, a set of MRI imaging data is accessed. The set of MRI imaging data may include at least a first volume acquired at a first time and a second volume acquired at a second time. Additional volumes may also be included in the set of MRI imaging data. At operation 604, at least one local contrast enhancement region is identified in at least two of the MRI images in the set of MRI imaging data. For instance, a local contrast enhancement region may be identified in the first volume and the second volume. At operation 606, contrast dynamics for the identified local contrast enhancement region is evaluated for the MRI volumes for which the local contrast enhancement region was identified. Evaluating the identified local contrast enhancement region for each MRI volume may include performing a colorization of each MRI volume by treating each MRI volume as if it were the peak enhancement volume. For example, colorization of the first MRI volume may be performed treating the first MRI volume as the peak enhancement volume, and the contrast dynamics for the identified local contrast enhancement region may be evaluated. The same can be done for the second MRI volume.

At operation 608, a peak enhancement volume is selected based on the evaluated contrast dynamics for the local contrast enhancement region. For example, selecting the peak enhancement volume may include a comparison of the evaluated contrast dynamics for the local contrast enhancement regions for each MRI volume in the set of MRI imaging data. At operation 610, colorization of the set of MRI imaging data is performed based on the peak enhancement volume selected in operation 608. The colorized set of MRI imaging data may then be displayed and/or stored locally or remotely.

Figure 7:
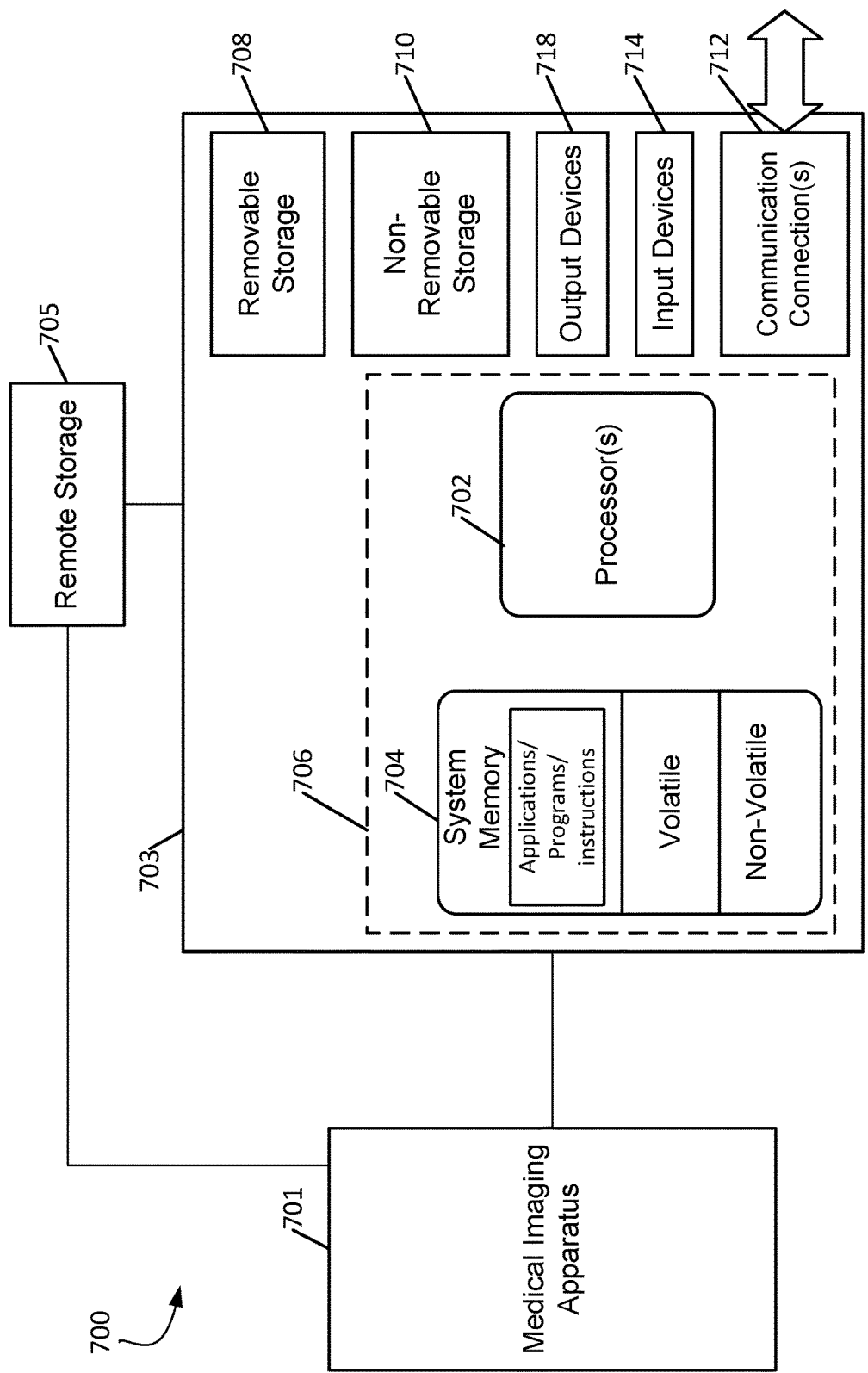
FIG. 7 depicts an example of a system for the medical imaging technologies discussed herein.

FIG. 7 illustrates one example of a system 700 having a medical imaging apparatus 701 and a suitable operating environment 703 in which one or more of the present examples of medical imaging may be implemented. The medical imaging apparatus 701 may be any medical imaging apparatus capable of dynamic imaging, such as an MRI apparatus. The medical imaging apparatus 701 may be in communication with the operating environment 703 and be configured to communicate medical images to the operating environment 703. The medical imaging apparatus 701 may also be in communication with remote storage 705 and be configured to communicate medical images to the remote storage 705. The remote storage 705 may also be in communication with the operating environment 703 and be configured to send stored medical images to the environment 703.

The operating environment 703 may be incorporated directly into the medical imaging apparatus 701, or may be incorporated into a computer system discrete from, but used to control, the imaging systems described herein. This is only one example of a suitable operating environment and is not intended to suggest any limitation as to the scope of use or functionality. Other computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 703 typically includes at least one processor 702 and memory 704. Depending on the exact configuration and type of computing device, memory 704 (storing, among other things, instructions to perform the image acquisition and processing methods disclosed herein) can be volatile (such as RAM), non-volatile (such as ROM, flash memory, etc.), or some combination of the two. This most basic configuration is illustrated in FIG. 7 by dashed line 706. Further, environment 703 can also include storage devices (removable, 708, and/or non-removable, 710) including, but not limited to, magnetic or optical disks, solid state devices, or tape. Similarly, environment 703 can also have input device(s) 714 such as touch screens, keyboard, mouse, pen, voice input, etc., and/or output device(s) 716 such as a display, speakers, printer, etc. Also included in the environment can be one or more communication connections 712, such as LAN, WAN, point to point, Bluetooth, RF, etc.

Operating environment 703 typically includes at least some form of computer readable media. Computer readable media can be any available media that can be accessed by processing unit 702 or other devices comprising the operating environment. As an example, the operating environment may include at least one processor 702 and memory 704 operatively connected to the at least one processor 702. The memory stores instructions, that when executed by the at least one processor cause the system to perform a set of operations, such as the operations described herein including the method operations discussed above.

By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 703 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are available in offices, enterprise-wide computer networks, intranets and the Internet.

In some embodiments, the components described herein comprise such modules or instructions executable by computer system 703 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 703 is part of a network that stores data in remote storage media for use by the computer system 703.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure. In addition, some aspects of the present disclosure are described above with reference to block diagrams and/or operational illustrations of systems and methods according to aspects of this disclosure. The functions, operations, and/or acts noted in the blocks may occur out of the order that is shown in any respective flowchart. For example, two blocks shown in succession may in fact be executrix or performed substantially concurrently or in reverse order, depending on the functionality and implementation involved.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art. Further, as used herein and in the claims, the phrase "at least one of element A, element B, or element C" is intended to convey any of: element A, element B, element C, elements A and B, elements A and C, elements B and C, and elements A, B, and C. Further, one having skill in the art will understand the degree to which terms such as "about" or "substantially" convey in light of the measurements techniques utilized herein. To the extent such terms may not be clearly defined or understood by one having skill in the art, the term "about" shall mean plus or minus ten percent.

Although specific embodiments are described herein, the scope of the technology is not limited to those specific embodiments. Moreover, while different examples and embodiments may be described separately, such embodiments and examples may be combined with one another in implementing the technology described herein. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method comprising:
   accessing a set of imaging data including first imaging data for a first time point, second imaging data for a second time point, and third imaging data for a third time point;
   identifying a first location of a region of interest (ROI) in the first imaging data;
   identifying a second location of the ROI in the second imaging data;
   identifying a third location of the ROI in the third imaging data;
   determining a plurality of differences between the identified locations, wherein the plurality of differences include a difference between:
      the first location and the second location;
      the first location and the third location; and
      the second location and the third location;
   based on the determined plurality of differences, selecting one of the first imaging data, the second imaging data, or the third imaging data as reference imaging data for motion correction; and
   performing motion correction for the set of imaging data with the selected reference imaging data.

2. The method of claim 1, wherein the set of imaging data is magnetic resonance imaging (MRI) data.

3. The method of claim 1, wherein the set of imaging data includes two-dimensional medical images and the locations of the ROI include a first coordinate corresponding to a first dimension and a second coordinate corresponding to a second dimension.

4. The method of claim 3, wherein determining the difference between the first location and the second location comprises:
   determining the difference between the first coordinate of the first location and the first coordinate of the second location; and
   determining the difference between the second coordinate of the first location and the second coordinate of the second location.

5. The method of claim 1, wherein the set of imaging data includes three-dimensional medical images and the locations of the ROI include a first coordinate corresponding to a first dimension, and a second coordinate corresponding to a second dimension, and a third coordinate corresponding to a third dimension.

6. The method of claim 5, wherein determining the difference between the first location and the second location comprises:
   determining the difference between the first coordinate of the first location and the first coordinate of the second location;
   determining the difference between the second coordinate of the first location and the second coordinate of the second location; and
   determining the difference between the third coordinate of the first location and the third coordinate of the second location.

7. The method of claim 1, wherein determining the difference between the first location and the second location comprises determining a distance between the first location and the second location.

8. The method of claim 1, further comprising acquiring the set of imaging data from a medical imaging apparatus.

9. The method of claim 1, further comprising receiving the set of imaging data from a remote storage source.

10. The method of claim 1, wherein the identification of the ROI is performed via computer-aided detection.

11. The method of claim 1, wherein the selected reference imaging data is based on an aggregate motion score based on the determined plurality of differences.

12. The method of claim 1, wherein the motion correction results in a motion corrected set of imaging data, and the method further comprises displaying at least a portion of the motion corrected set of imaging data.

13. The method of claim 1, wherein the ROI is a centroid of a breast.

14. A system comprising:
   a display;
   at least one processor; and
   memory storing instructions that, when executed by the at least one processor, cause the system to perform a set of operations, the set of operations comprising:
      accessing a set of imaging data including first imaging data for a first time point, second imaging data for a second time point, and third imaging data for a third time point;
      identifying a first location of a region of interest (ROI) in the first imaging data;
      identifying a second location of the ROI in the second imaging data;
      identifying a third location of the ROI in the third imaging data;
      determining a plurality of differences between the identified locations, wherein the plurality of differences include a difference between:
         the first location and the second location;
         the first location and the third location; and
         the second location and the third location;
      based on the determined plurality of differences, selecting one of the first imaging data, the second imaging data, or the third imaging data as reference imaging data for motion correction;
      performing motion correction for the set of imaging data with the selected reference imaging data; and
      displaying imagery based on the motion corrected set of imaging data on the display.

15. The system of claim 14, further comprising a medical imaging apparatus and the set of operations further comprise acquiring the set of imaging data from the medical imaging apparatus.

16. The system of claim 15, wherein the medical imaging apparatus is a magnetic resonance imaging (MRI) machine and the imaging data includes MRI volumes.

17. The system of claim 14, wherein the set of imaging data includes two-dimensional medical images and the locations of the ROI include a first coordinate corresponding to a first dimension and a second coordinate corresponding to a second dimension, and wherein determining the difference between the first location and the second location comprises:

determining the difference between the first coordinate of the first location and the first coordinate of the second location; and determining the difference between the second coordinate of the first location and the second coordinate of the second location.

18. The system of claim 14, wherein the set of imaging data includes three-dimensional medical images and the locations of the ROI include a first coordinate corresponding to a first dimension, and a second coordinate corresponding to a second dimension, and a third coordinate corresponding to a third dimension, and determining the difference between the first location and the second location comprises:

determining the difference between the first coordinate of the first location and the first coordinate of the second location;

determining the difference between the second coordinate of the first location and the second coordinate of the second location; and determining the difference between the third coordinate of the first location and the third coordinate of the second location.

19. The system of claim 14, further comprising wherein determining the difference between the first location and the second location comprises determining a distance between the first location and the second location.

\* \* \* \* \*